US012653941B2

(12) United States Patent
Kucklick

(10) Patent No.: US 12,653,941 B2
(45) Date of Patent: Jun. 16, 2026

(54) MINIATURIZED PUMP ASSEMBLY FOR AN ENDOSCOPE

(71) Applicant: PSIP2 LLC, Manchester, NH (US)

(72) Inventor: Theodore R. Kucklick, Scotts Valley, CA (US)

(73) Assignee: PSIP2 LLC, Manchester, NH (US)

( * ) Notice: Subject to any disclaimer, the term of this patent is extended or adjusted under 35 U.S.C. 154(b) by 321 days.

(21) Appl. No.: 18/477,914

(22) Filed: Sep. 29, 2023

(65) Prior Publication Data

US 2024/0108795 A1 Apr. 4, 2024

Related U.S. Application Data

(60) Provisional application No. 63/377,806, filed on Sep. 30, 2022.

(51) Int. Cl.
*A61B 1/00* (2006.01)
*A61B 1/317* (2006.01)
*A61M 1/00* (2006.01)
(52) U.S. Cl.
CPC .......... *A61M 1/80* (2021.05); *A61B 1/00103* (2013.01); *A61B 1/00135* (2013.01); *A61B 1/317* (2013.01)

(58) Field of Classification Search
CPC .......... A61M 1/80; A61M 1/774; A61M 1/74; A61B 1/00103; A61B 1/00135; A61B 1/317; A61B 1/015; A61B 1/00066; A61B 1/0052
See application file for complete search history.

(56) References Cited

U.S. PATENT DOCUMENTS

| | | | |
|---|---|---|---|
| 2008/0154095 A1 | 6/2008 | Stubkjaer et al. | |
| 2014/0140815 A1 | 5/2014 | Shener-Irmakoglu et al. | |
| 2021/0361311 A1 | 11/2021 | Truckai et al. | |

FOREIGN PATENT DOCUMENTS

| | | |
|---|---|---|
| CN | 203988374 | 12/2014 |
| CN | 107374680 | 11/2017 |

OTHER PUBLICATIONS

International Search Report and Written Opinion dated Jan. 22, 2024 from IA PCT/US2023/075501.

*Primary Examiner* — Timothy J Neal
(74) *Attorney, Agent, or Firm* — Bond Schoeneck & King PLLC

(57) ABSTRACT

A miniaturized pump assembly for inflow and outflow of fluid gas and smoke during arthroscopic and laparoscopic surgery.

12 Claims, 7 Drawing Sheets

MINIATURIZED PUMP ASSEMBLY FOR AN ENDOSCOPE

This application claims priority to U.S. Provisional Application 63/377,806 filed Sep. 30, 2022.

FIELD OF THE INVENTIONS

The inventions described below relate to the field of arthroscopic and laparoscopic surgery and more specifically, to miniaturized pump assemblies for inflow and outflow of fluid, gas and smoke during arthroscopic and laparoscopic surgery.

BACKGROUND OF THE INVENTIONS

Endoscopes are used in both arthroscopic and laparoscopic procedures. Arthroscopy is a minimally invasive procedure for treating joint pathology and is a superior alternative to open joint arthrotomy. Laparoscopic surgery is also a minimally invasive surgical technique that involves making small incisions in the abdomen and inserting laparoscopes and cameras to perform surgical procedures inside the abdominal cavity. These procedures require large volumes of irrigation fluid to be delivered to the surgical site in order to perform the procedures. A pump system for supplying or evacuating fluids from the surgical site are required to complete the procedures. The pump system within an endoscopic system is responsible for the controlled delivery of fluids through a patient's body. Typical pump systems for such procedures are located in costly capital equipment towers next to the surgical device or endoscope. The equipment towers are cumbersome and generate lots of waste. What is needed is an instrument system that incorporates the pump within the endoscope in order to eliminate the need for a separate fluid pump and all of the expensive pump tubing and cassettes associated with the pump in order to increase performance and reduce waste.

SUMMARY

The devices and methods described below provide for easy pump irrigation of an endoscope for supplying fluid to and evacuating fluid from the endoscope via a miniaturized pump assembly. The pump assembly can be housed within a handle of a digital endoscope or can can be used without an endoscope as an inline pump to replace a conventional fluid pump and tubing setup. The pump assembly can include a first inflow pump and a second outflow pump connected in series to each other. The pump assembly can connect to an inflow and outflow sheath of a digital endoscope. Alternatively, the pump assembly can include a first inflow pump attached in series to a second inflow pump that is contained within a housing. This pump assembly can connect to an outflow sheath outside of a digital endoscope. The pump assembly may be modular or a unitary body construction. The modular system includes at least one inflow pump and either a second inflow pump or an outflow pump assembled in any combination thereof.

The assembly can include a pressure sensor that measures the pressure in a surgical workspace. The sensor sends the pressure reading to a pump controller board configured to maintain a fluid operating parameter delivered to the pump assembly within a pre-determined range. The endoscope may also include a digital endoscope controller for receiving and processing images from the surgical workspace and transmitting them to a monitor to display. The endoscope incorporates the entire pump assembly into a handle housing. Operation of the pump assembly within the housing provides the advantage that it greatly simplifies the surgical setup and eliminates the need for costly capital equipment towers. In addition, the entire pump assembly can be single use disposable for further efficiency.

DETAILED DESCRIPTION OF THE INVENTIONS

Figure 1A:
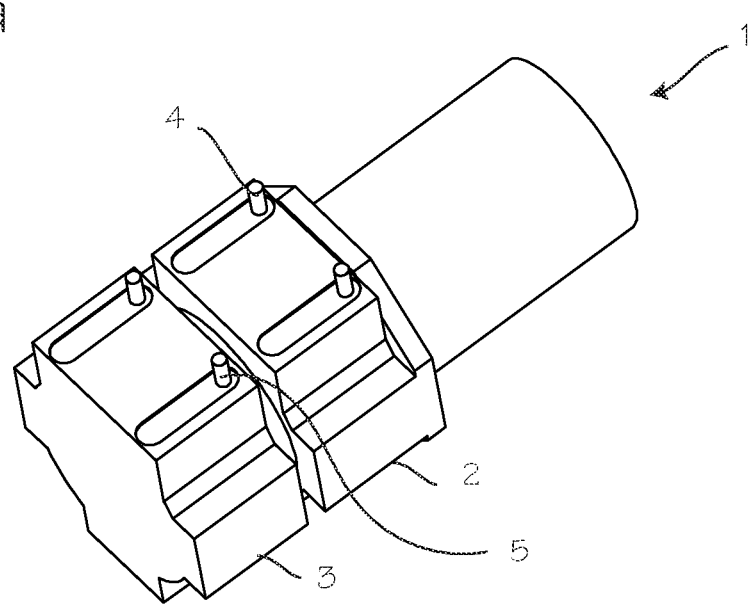
FIGS. 1a and 1b and 1c are miniaturized pump assemblies for use with an endoscope.
Figure 1B:
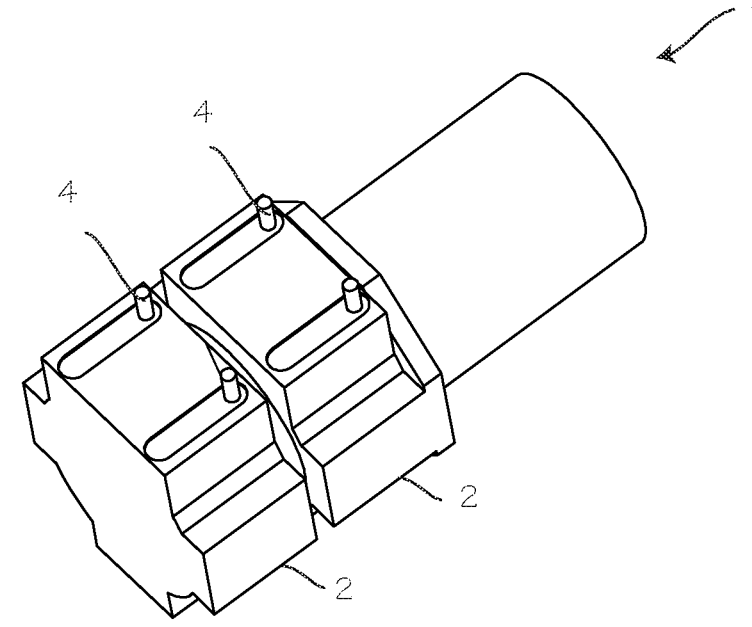
Figure 1C:
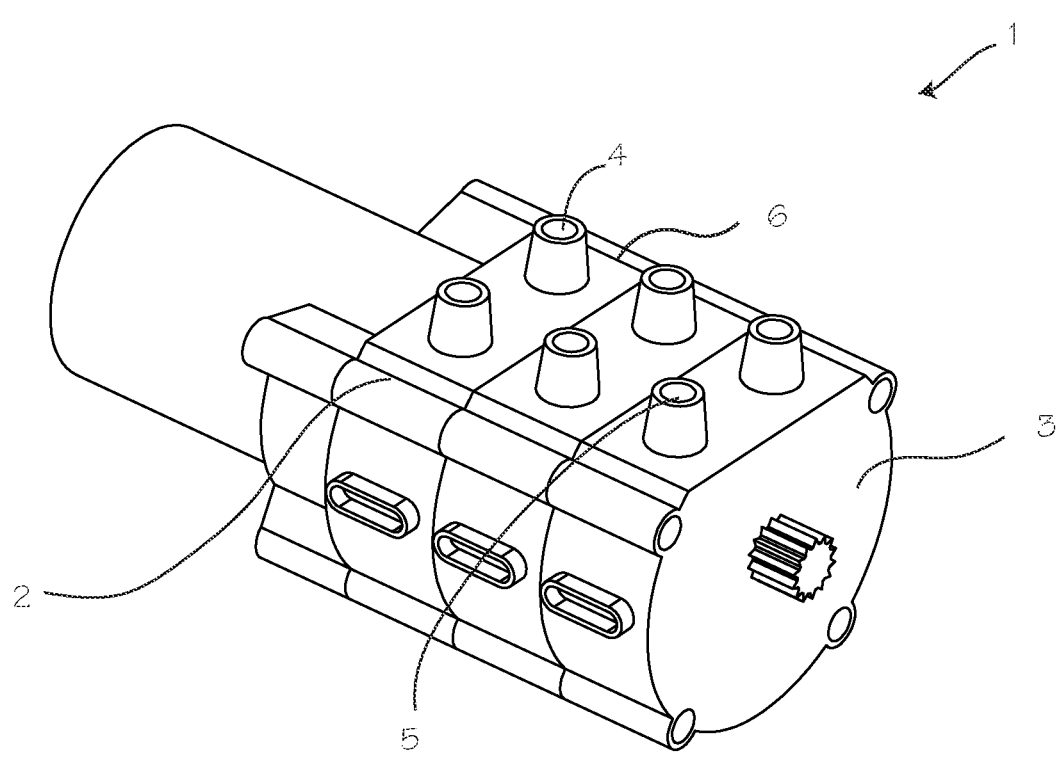

FIG. 1a illustrates a miniaturized pump assembly 1 for use with an endoscope. The pump assembly has a distal end and a proximal end and includes a first pump 2 and a second pump 3 connected in series to each other. The first pump is an inflow pump and the second pump is an outflow pump. The first inflow pump includes at least one fluid inlet port 4 for introduction of fluid from a fluid source. The second outflow pump has a fluid output port 5 for transmission of fluids out of the proximal end of the pump assembly to a drain. This configuration allows for simultaneous controlled inflow and outflow of the pump assembly. The inflow pump inlet port is formed on a surface of the inflow pump with a bore providing a fluid pathway to the fluid output port of the outflow pump. Flow can pass through the inflow pump in either direction, so that either end can serve as the inlet or the outlet, or, correspondingly, the proximal end and the distal end. Flow through the pump assembly follows the path through the opening of inlet port, radially through a wall of the inflow pump and exits to the outflow pump via the fluid output port. The fluid output port is formed on the surface of the outflow pump with a bore providing a fluid pathway to exit the outlet pump back out of the proximal end of the pump assembly to drain. The entire pump assembly is contained within a handle housing. FIG. 1b illustrates a miniaturized pump assembly where the first and second pumps are both inflow pumps 2 connected in series to each other. In this configuration, the outflow is from a separate accessory outflow cannula or an outflow sheath on a digital endoscope. FIG. 1c illustrates a pump assembly that includes multiple inflow and outflow pumps) and also a manifold 6 for inflow and outflow of fluid into the plum assembly.

Figure 2:
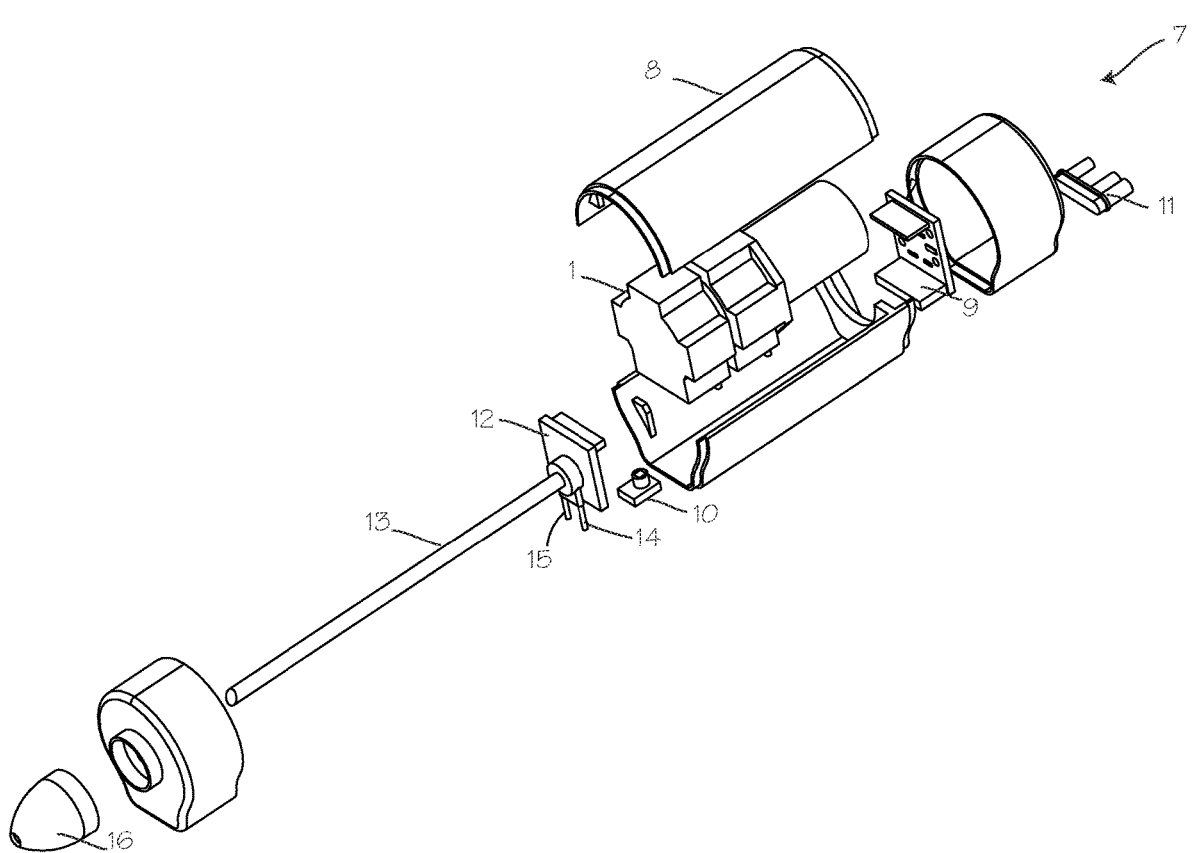
FIG. 2 is an exploded view of an endoscope with a pump assembly contained within a handle.

FIG. 2 is an exploded view of a digital arthroscope 7 with a pump assembly 1 contained within a handle. The handle includes a housing 8 having a distal end, a proximal end and an inner diameter sized and dimensioned to be removably disposed over an arthroscopic instrument and the pump assembly. The pump assembly is contained within the housing and can be operably connected to a pump controller 9 at an end of the pump assembly and a pressure sensor 10 at an end of the pump assembly. The pump assembly may also include a fluid and electrical connector 11 that extends from the proximal end of the arthroscope and is connected to a power supply. The pressure sensor is adjacent to a scope controller 12 affixed to a digital chip scope 13. The scope controller further includes two projections having a scope fluid inflow sheath 14 for introduction or inflow of fluid into the inflow pump from the inflow sheath and a fluid outflow sheath 15 for the expulsion or outflow of fluid to drainage from the second outflow pump. The digital scope has a distal tip that projects from the scope controller from the distal end of the arthroscope to capture images from the distal tip at the surgical site. A cap 16 can optionally cover the digital chip scope. The pump assembly and its flow path are configured to provide a fluid channel for pressurized fluid from fluid or air introduced to the inflow pump via the fluid inflow sheath and out through the pump assembly from the cannula outflow sheath via the outlet pump. The pump assembly 1 can be an inflow and outflow pump including both an inflow pump and an outflow pump connected in series to each other. Alternatively, the pump assembly can be an inflow only pump including two inflow pumps connected in series to each other where the outflow flows through an outflow sheath contained on a digital scope.

The pump assembly 1 generates the mechanical force needed to generate the endoscope's operation. The pump assembly generates flow of fluids or gas and is configured to control the flow rate, pressure and volume of the fluid or gas through the inflow pump and the outflow pump. The pump assembly can include a single pump or double pump system that operates to deliver flow in a first flow direction. The inflow pump and the outflow pump can be operated by the pump controller configured to maintain a fluid operating parameter delivered by the pump assembly within a predetermined range. It may be any positive displacement fluid module, peristaltic pumps or syringe-based mechanism for fluid management. For example the inflow and outflow pumps can be a peristaltic pump, lobe gear, Roots style pump, centrifugal pump, axial flow pump, diaphragm pump or impeller pump. The inflow and outflow pump platforms operates at between 5 mm/HG to 150 mm/HG pressure from 5 mL/minute to 2 L/minutes of flow that can be contained or fit within an endoscope handle. The pumps can include any pump that is operable to flow fluids or insufflation gases or remove smoke from the system may be used. The pumps can be powered from the same power source as the endoscope, or its power supply or a battery power pack. The pumps can include a single inflow pump for inflow, a double pump with inflow and outflow, a separate inflow pump and an outflow pump. The pumps can be any suitable pump for indications such as arthroscopy and urology or one or more pump modules that can pump in gas and excavate smoke for indications such as laparoscopy. The pump assembly is configured to fit inside an endoscopic handle. The length of the pump assembly is between 5 cm to 10 cm centimeters and the diameter in the range of 5 mm to 10 mm millimeters to ensure can fit through narrow channels and work within the constraints of endoscopic instruments. The pump assembly can also be controlled and operated wirelessly.

The pressure sensor 10 is operable to measure the pressure at the surgical site to be able to calibrate the pump assembly 1 pressure and flow accuracy by adjusting the fluid introduction to the first inflow pump 2 or the expulsion of fluid from the second outflow pump 5 to maintain the pressures within a within a predetermined range. The pressure sensor is operable to measure the pressure exerted by the endoscope on the tissue being examined within the surgical space. The pressure sensor then generates an electrical signal proportional to the pressure measurement and outputs the digital signal and transmits the sensor data to an external monitor for display. A feedback control system within the pump controller is operable to monitor the actual pressure exerted by the endoscope, compare it to predetermined acceptable ranges and transmit a signal to the pump controller to adjust applied force of the pump assembly to come within predetermined range. The pump controller 9 keeps the pressure within a predetermined range based on a control algorithm program. The pressure sensor may be operated wired or wirelessly via a wireless protocol. Usage data may be captured and stored in a database for later analysis. The system may also include procedure templates stored in a look up table for presets for different procedures such as knee, shoulder or hip arthroscopy as well as the ability to store custom user preference settings. Fluid serves many purposes to clear debris or blood to provide a clear view for endoscopist, enhancing image or facilitate therapeutic interventions.

The inflow pump 2 function is to regulate the flow of sterile fluids, such as saline solution, through the endoscope's handle. The inflow pump prevents backflow of fluids and is configured to only allow introduction of fluid into working channels when desired. Fluid or gas flows through the input pump and introduced to the outflow pump 3. The outflow pump is the exhaust or suction portion that controls the removal of gas, fluid or debris through the endoscopes working channels. The outflow pump may include a pressure limiting valve or pressure relief valve or additional sensors or pressure gauges to regulate the force applied to remove the fluid or gas from the pump assembly. The inflow and outflow pumps may include an internal solenoid controller clutch for independent operation or alternatively include a clutch positioned between the flow modules. In a pump assembly including two inflow pumps connected in series to each other, the outflow flows through an outflow sheath contained on a digital scope.

The digital scope controller 12 acquires images or signals from a camera sensor inside the digital chip scope 13. The digital scope controller converts the signal or image into a processed digital image and transmits the processed signal to a monitor on which it is displayed. The digital scope controller also includes a user interface for controlling aspects of the image such as zooming, panning, adjusting brightness and contrast.

The fluid inflow sheath 14 is in fluid communication with the inflow pump contained within the endoscope housing. The fluid outflow sheath 15 is also in fluid communication with the distal tip of the pump assembly and is positioned adjacent to the inflow sheath. It serves the purpose of removing fluid, debris or air from the surgical site. The outflow sheath is connected to a suction device such as a vacuum pump or suction system.

Figure 3:
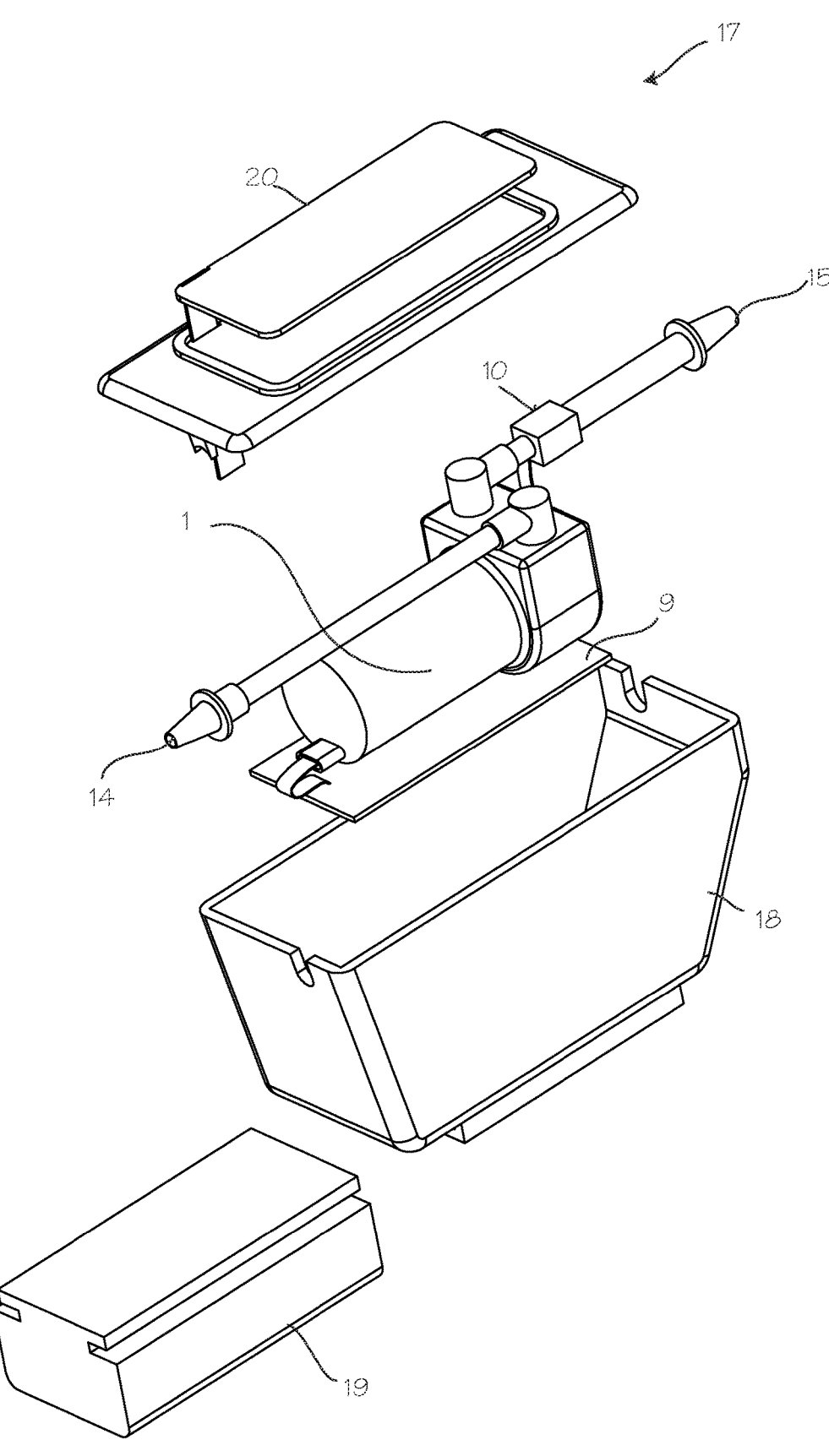
FIG. 3 is an exploded view of a disposable pump assembly.

FIG. 3 is an exploded view of a disposable pump assembly 17. The entire pump assembly 1 is contained within a housing 18 that can be used with an endoscope. The pump assembly is contained within the housing and can be operably connected to a pump controller 9 and a pressure sensor 10. A fluid inflow sheath 14 is in fluid communication with an inflow pump contained within the housing and a fluid outflow sheath 15 is in fluid communication with an outflow pump within the assembly. The pump assembly may be operable connected to a power source such as a battery or DC motor or transformer 19. The disposable pump assembly can also include a pressure readout and control LCD screen 20. The fluid inflow sheath, pump assembly and fluid outflow sheaths are configured in-line with each other. The pump assembly can include at least one inflow pump and at least one outflow pump in series with each other. Alternatively, the pump assembly can include a plurality of inflow pumps in series with each other or a combination of a plurality of inflow and outflow pumps. The entire pump assembly is sealed within the housing, sterilizable and disposable after a single use.

Figure 4:
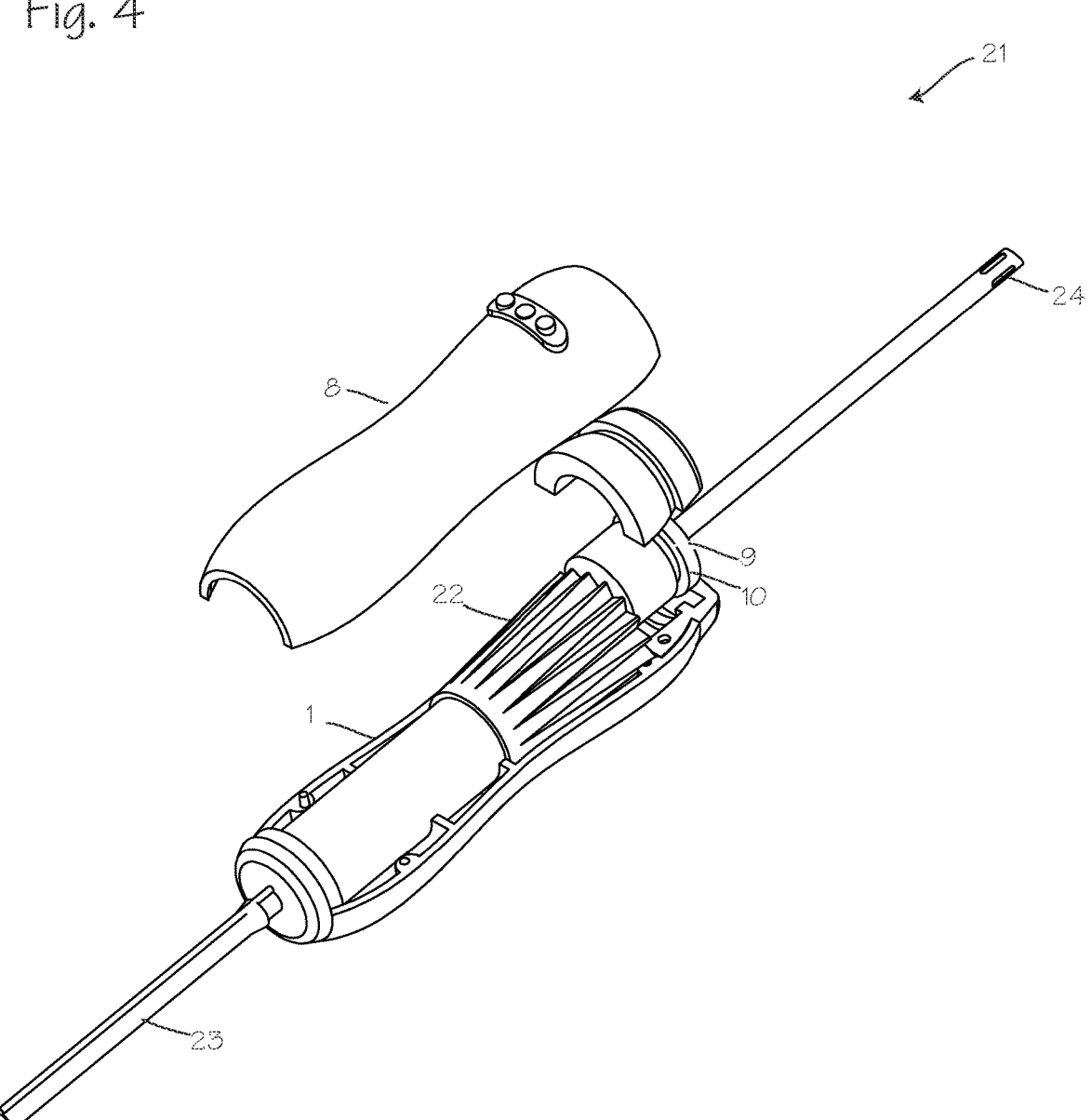
FIG. 4 is an exploded view of a digital laparoscope with a pump assembly contained within a handle.

FIG. 4 is an exploded view of a digital laparoscope 21 with a pump assembly contained within the handle. The components are the same as the endoscopic handle and can also include a smoke filter 22. A laparoscopic handle includes a housing 8 having a distal end, a proximal end and an inner diameter sized and dimensioned to be removably disposed over a laparoscopic instrument and the pump assembly. The pump assembly is contained within the housing and can be operably connected to a pump controller 9 and a pressure sensor 10. The smoke filter is positioned between the pump assembly and the pressure sensor within the housing. The pump assembly may also include a power and data cable 23 that is connected to a power supply. The pressure sensor is adjacent to a scope controller 12 affixed to a digital chip scope 13. The scope controller further includes either a single gas inflow and smoke removal outflow sheath 24 for introduction or inflow of fluid into the sheath and outflow of smoke from the sheath. Alternatively, the sheath can be a smoke outflow removal sheath that is used in combination with a separate accessory gas inflow sheath such as a trocar or through the digital scope. The smoke filter in the handle eliminates the need for a separate smoke filter box. Suction of the smoke removal may be from wall suction within the scope wall or a disposable suction pump motor in the handle of the digital scope. The pump assembly and its flow path are configured to provide a channel for pressurized fluid from fluid or smoke introduced to the inflow pump and out outflow the fluid or smoke through the inflow/outflow sheath. The pump assembly includes a modular or unitary pump assembly that is operable to flow insufflation gases and remove smoke from the system. The pump system can include a single pump or double pump system, that operates to deliver flow and operates in pressure range of 6 mmHG to 15 mmHG with flow rate of 1 to 30 liters per minute.

Figure 5:
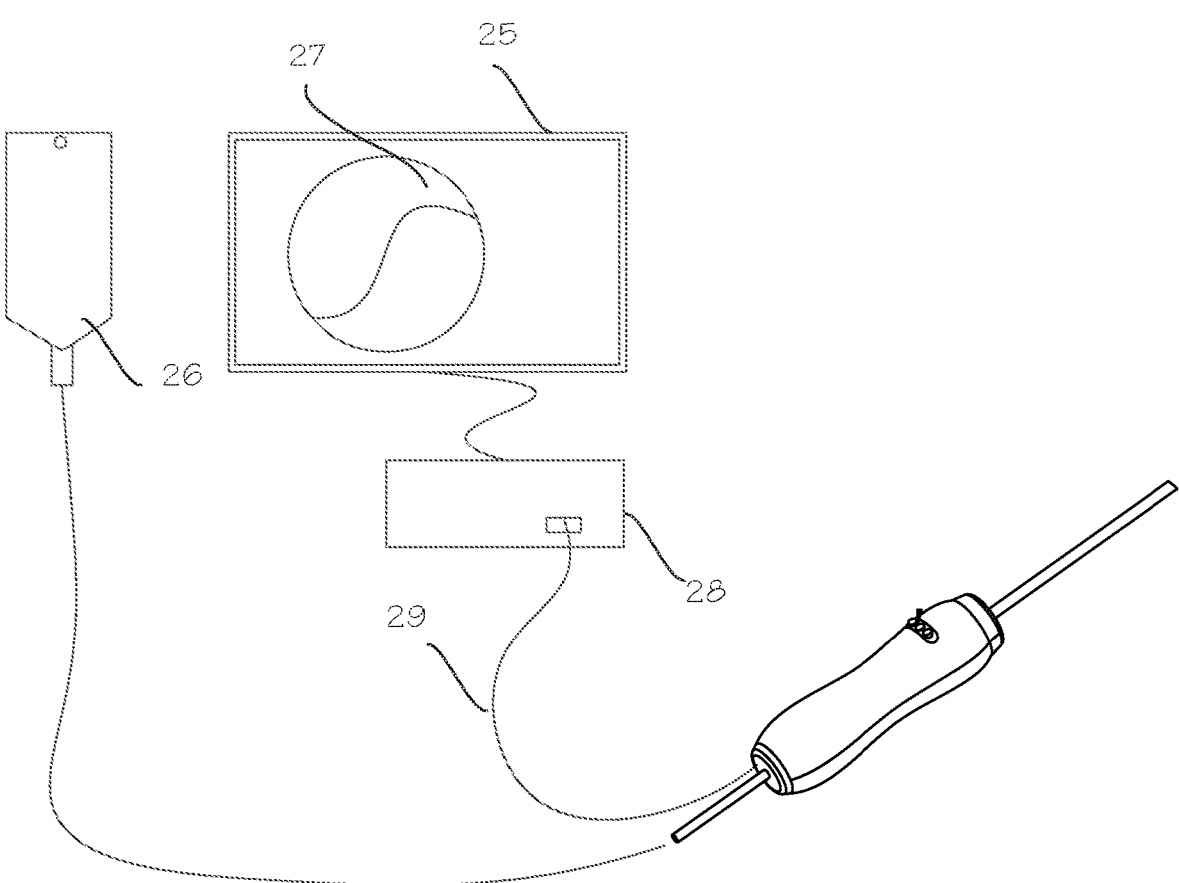
FIG. 5 illustrates an endoscope in use during an arthroscopic procedure.

FIG. 5 illustrates an endoscope in use during an arthroscopic procedure. An arthroscope is inserted into a handle that includes the desired pump assembly in communication with a monitor 25, scope controller and pump controller. Fluid immersion from a fluid bag 26 begins for the desired procedure. The fluid is introduced into the handle and flows through the inflow segment and is introduced via the fluid outlet port into the outflow segment from the distal end of the arthroscope to the desired surgical space. Fluid is then returned via a fluid outflow sheath to drainage. The pressure sensor senses the fluid pressure within the surgical space. The pressure sensor then generates an electrical signal proportional to the pressure measurement and outputs the digital signal and transmits the sensor data 27 to an external monitor for display. A feedback control system within the pump controller is operable to monitor the actual pressure exerted by the arthroscope, compare it to predetermined acceptable ranges and transmit a signal to the pump controller to adjust applied force of the pump assembly to come within predetermined range. The power and data connection are intermediately connected to the monitor via a power supply, pump control box and digital scope image processing box 28. The pump assembly also includes a power cord 29 that extends from the distal end of the arthroscope and is operably connected to a power supply to power the system.

Figure 6:
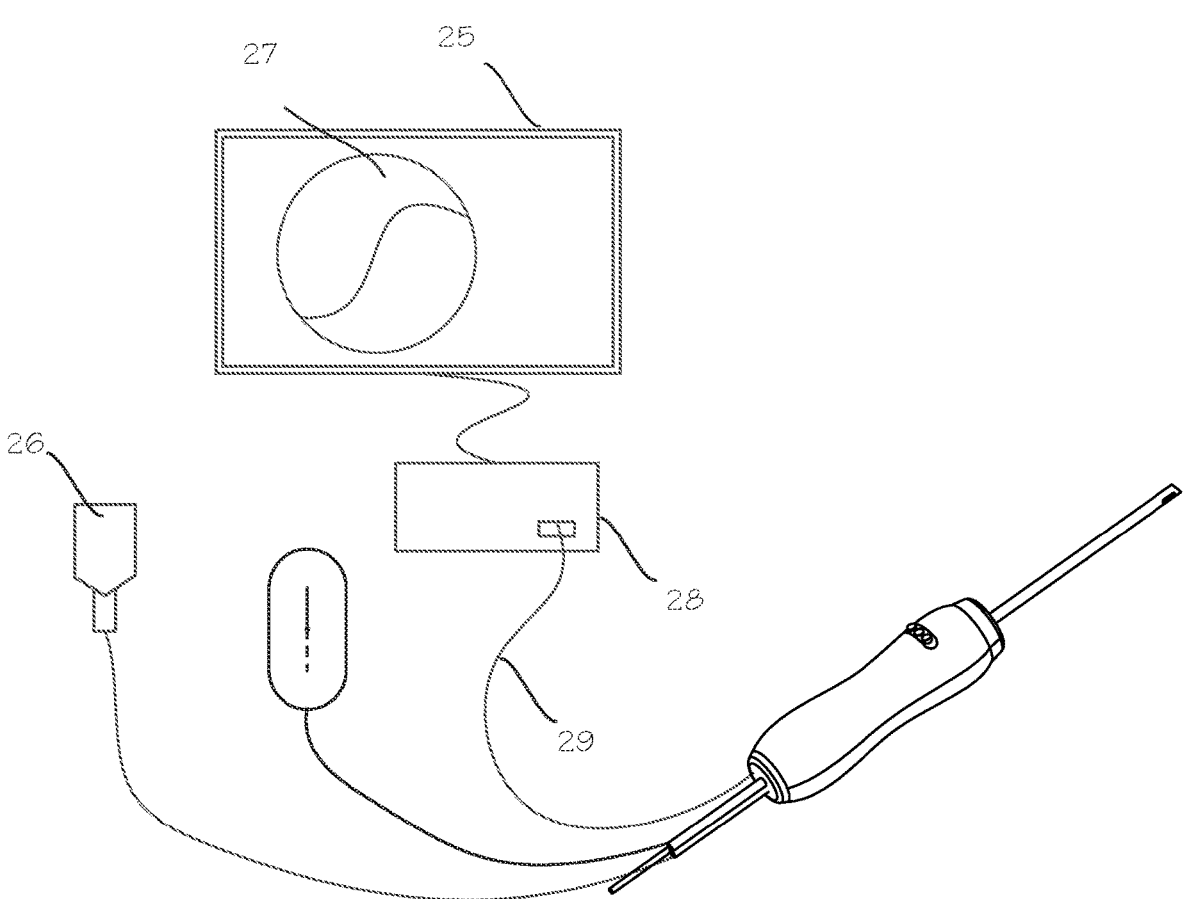
FIG. 6 illustrates an endoscope in use during a laparoscopic procedure.

FIG. 6 illustrates a laparoscope in use during a laparoscopic procedure. A laparoscope is inserted into a handle that includes the desired pump assembly in communication with a monitor 25, scope controller and pump controller. Fluid from a fluid bag begins for the desired procedure. The fluid is introduced into the handle and flows through a inflow/outflow tube and flows through a laparoscopic wall suction of a smoke removal tube and is exited from the same inflow/outflow tube. The pressure sensor 10 senses the fluid pressure within the surgical space. The pressure sensor then generates and electrical signal proportional to the pressure measurement and outputs the digital signal and transmits the sensor data 27 to an external monitor for display. A feedback control system within the pump controller is operable to monitor the actual pressure exerted by the laparoscope, compare it to predetermined acceptable ranges and transmit a signal to the pump controller to adjust applied force of the pump assembly to come within predetermined range. The power and data connection are intermediately connected to the monitor via a power supply, pump control box and digital scope image processing box 28. The pump assembly also includes a power cord 29 that extends from the distal end of the arthroscope and is operably connected to a power supply to power the system.

While the preferred embodiments of the devices and methods have been described in reference to the environment in which they were developed, they are merely illustrative of the principles of the inventions. The elements of the various embodiments may be incorporated into each of the other species to obtain the benefits of those elements in combination with such other species, and the various beneficial features may be employed in embodiments alone or in combination with each other. Other embodiments and configurations may be devised without departing from the spirit of the inventions and the scope of the appended claims.

I claim:

1. An arthroscopic surgical pump system comprising:
a housing characterized by a distal end, a proximal end, and an inner diameter sized and dimensioned to be removably disposed over an arthroscopic instrument; and
a modular pump assembly having a distal end and a proximal end, comprising:
a inflow pump having at least one fluid inlet port for introduction of fluid from a fluid source;
an outflow pump connected in series to the inflow pump and having at least one fluid output port for transmission of fluids out of the outflow pump;
a pressure sensor contained at an end of the pump assembly and operable to obtain pressure readings and transmit the readings; and
a pump controller operable to receive the readings from the pressure sensor to adjust the fluid introduction to the inflow pump or the expulsion of fluid from the outflow pump to maintain the pressures within a predetermined range; and
wherein the modular pump assembly is entirely contained within the housing.

2. The arthroscopic surgical pump system of claim 1, further comprising a digital scope and a scope controller operably connected to the modular pump assembly.

3. The arthroscopic surgical pump system of claim 2, wherein the scope controller further includes an inflow sheath and an outflow sheath configured for introduction of fluid to the inflow pump and removal of fluid from the outflow pump.

4. The arthroscopic surgical pump system of claim 1, wherein the inflow pump and the outflow pump are peristaltic pumps.

5. The arthroscopic surgical pump system of claim 1, wherein the inflow pump and the outflow pump operate at between 5 mm/HG and 150 mm/HG pressure with flow rates between 5 mL/minute and 2 L/minute.

6. The arthroscopic surgical pump system of claim 1, wherein the modular pump assembly is disposable.

7. An arthroscopic surgical pump system comprising:

a housing characterized by a distal end, a proximal end, and an inner diameter sized and dimensioned to be removably disposed over an arthroscopic instrument and including an outflow sheath within the housing; and a modular pump assembly having a distal end and a proximal end, comprising:

a first inflow pump having at least one fluid inlet port for introduction of fluid from a fluid source;

a second inflow pump connected in series to the first inflow pump;

a pressure sensor contained at an end of the pump assembly and operable to obtain pressure readings and transmit the readings;

a outflow pump connected in series to the first and second inflow pumps and having at least one fluid output port for transmission of fluids out of the outflow pump; and a pump controller board operable to receive the readings from the pressure sensor to adjust the fluid introduction to either the first or second inflow pump to maintain the pressures within a predetermined range; and wherein the modular pump assembly is entirely contained within the housing.

8. The arthroscopic surgical pump system of claim 7, wherein the scope controller further includes a cannula inflow sheath and an outflow sheath configured for introduction of fluid to the first inflow pump and removal of fluid from the outflow pump.

9. The arthroscopic surgical pump system of claim 8, wherein the inflow pump and the outflow pump are peristaltic pumps.

10. The arthroscopic surgical pump system of claim 7, wherein the inflow pumps and the outflow pump operate at a pressure of between 5 mm/HG and 150 mm/HG and a flow rate of between 5 mL/minute and 2 L/minute.

11. The arthroscopic surgical pump system of claim 7, wherein the modular pump assembly is disposable.

12. The arthroscopic surgical pump system of claim 7, further comprising a scope controller operably connected to the modular pump assembly.

* * * * *